United States Patent
Torstensen

(10) Patent No.: US 11,896,514 B2
(45) Date of Patent: Feb. 13, 2024

(54) OSTOMY PRODUCT WITH MESH INTERNAL COLLECTION MEMBER FOR GAS PASSAGE

(71) Applicant: Hollister Incorporated, Libertyville, IL (US)

(72) Inventor: Jan Torstensen, Virum (DK)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 17/835,655

(22) Filed: Jun. 8, 2022

(65) Prior Publication Data

US 2022/0401251 A1    Dec. 22, 2022

Related U.S. Application Data

(60) Provisional application No. 63/213,418, filed on Jun. 22, 2021.

(51) Int. Cl.
| | |
|---|---|
| A61F 5/44 | (2006.01) |
| A61F 5/441 | (2006.01) |
| A61F 5/448 | (2006.01) |
| A61F 2/00 | (2006.01) |

(52) U.S. Cl.
CPC ............ *A61F 5/4407* (2013.01); *A61F 5/441* (2013.01); *A61F 5/448* (2013.01); *A61F 2/0063* (2013.01)

(58) Field of Classification Search
CPC ...... A61F 5/4407; A61F 5/441; A61F 2/0063; A61F 5/445–543; A61F 2005/4455–4495
See application file for complete search history.

(56) References Cited

U.S. PATENT DOCUMENTS

| | | | | |
|---|---|---|---|---|
| 8,657,799 | B2* | 2/2014 | Carrubba | A61F 5/445 |
| | | | | 604/318 |
| 8,821,465 | B2* | 9/2014 | Hanuka | A61F 5/4407 |
| | | | | 604/333 |
| 2006/0200101 | A1* | 9/2006 | Mullejans | A61F 5/448 |
| | | | | 604/339 |
| 2013/0079737 | A1* | 3/2013 | Hanuka | A61F 5/449 |
| | | | | 604/318 |
| 2021/0369485 | A1* | 12/2021 | Evans | A61F 5/4404 |
| 2023/0074823 | A1* | 3/2023 | Hoggarth, Jr. | A61F 5/441 |

* cited by examiner

*Primary Examiner* — Erich G Herbermann
*Assistant Examiner* — Peter Daniel Smith
(74) *Attorney, Agent, or Firm* — Levenfeld Pearlstein, LLC

(57) ABSTRACT

An ostomy pouch has a body side wall and a distal side wall defining a collection chamber. An opening is provided in the body side wall. A barrier is operably mounted to the body side wall over the opening. The barrier has an inlet opening. An internal collection member is mounted to the barrier. The internal collection member includes a tubular net having a first open end and a second closed end, and a ring-shaped capsule for storing the net inside the capsule in a collected manner. The ring-shaped capsule has an open central region and is mounted to the barrier with the capsule open central region and the barrier inlet opening aligned with one another to define a pouch inlet. The capsule extends into the pouch collection chamber and the first open end of the net is mounted to the capsule overlying the pouch inlet. Excretion is inlet to the pouch and is discharged into the net, paying out the net.

6 Claims, 3 Drawing Sheets

OSTOMY PRODUCT WITH MESH INTERNAL COLLECTION MEMBER FOR GAS PASSAGE

BACKGROUND

The present disclosure pertains to an ostomy product, such as an ostomy pouch for collecting biological excretions (such as excretions from a surgically-created stoma). More particularly, the present disclosure pertains to an ostomy product, such as an ostomy pouch with an internally located mesh collection member to facilitate gas passage that reduces the likelihood of filter clogging, and reduces the likelihood of "pancaking" or ballooning of the ostomy product walls.

Ostomy users have experienced clogging of ostomy pouch filters when solid excretion contacts and/or covers the filter element. This can result is preventing gas from exhausting from the pouch. This can cause ballooning of the pouch as it fills with gas that cannot escape.

Pancaking occurs when a vacuum or near vacuum is present in the pouch causing the pouch walls to stick together, and the excretions collecting on the inside of the pouch wall, around the barrier near the pouch inlet. When this occurs, the excretions stick to the pouch walls and do not fall to the bottom of the pouch resulting in improper functioning of the ostomy appliance.

Any of these phenomena can cause discomfort and/or embarrassment for the user in that the pouch may not properly fit on the user, may be visible, or may emit gases at an undesirable time and/or location. Moreover, these phenomena can also result in inefficient use of the ostomy pouch.

Accordingly, there is a need for a device in an ostomy product that prevent excretions from clogging the product filter. More desirably still, such as device directs excretions away from the filter, thus preventing ballooning or pancaking of the pouch walls.

SUMMARY

An ostomy device such as an ostomy pouch for collecting bodily excretions has a body side wall and a distal side wall defining a collection chamber. An opening is provided in the body side wall and a barrier is operably mounted to the body side wall over the opening. The barrier has an inlet opening.

An internal collection member is mounted to the barrier. The internal collection member includes a tubular net having a first open end and a second closed end, and a ring-shaped capsule for storing the net. The net can be stored in the capsule in a collected manner.

The ring-shaped capsule has an open central region and is mounted to the barrier with the capsule open central region and the barrier inlet opening aligned with one another to define a pouch inlet. The capsule extends into the pouch collection chamber, with the first open end of the net mounted to the capsule to overlie the pouch inlet. As excretion is inlet to the pouch and is discharged into the net, the excretion pays out the net.

In an embodiment, the capsule includes a circumferential opening, and the net is paid out from the capsule through the opening. The capsule can include a front wall in which the circumferential opening is formed and a rear wall. The rear wall can be flat to facilitate mounting to the barrier.

In an embodiment, the net is formed from a mesh. The first open end of the net can be secured to an interior surface of the capsule. The pouch can further include a filter, such that gas inlet to the pouch with the excretion passes through the net and is discharged from the pouch through the filter. The filter can be, for example, on the distal side wall Other aspects and advantages will become more apparent from the following detailed description when taken in conjunction with the accompanying drawings.

DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
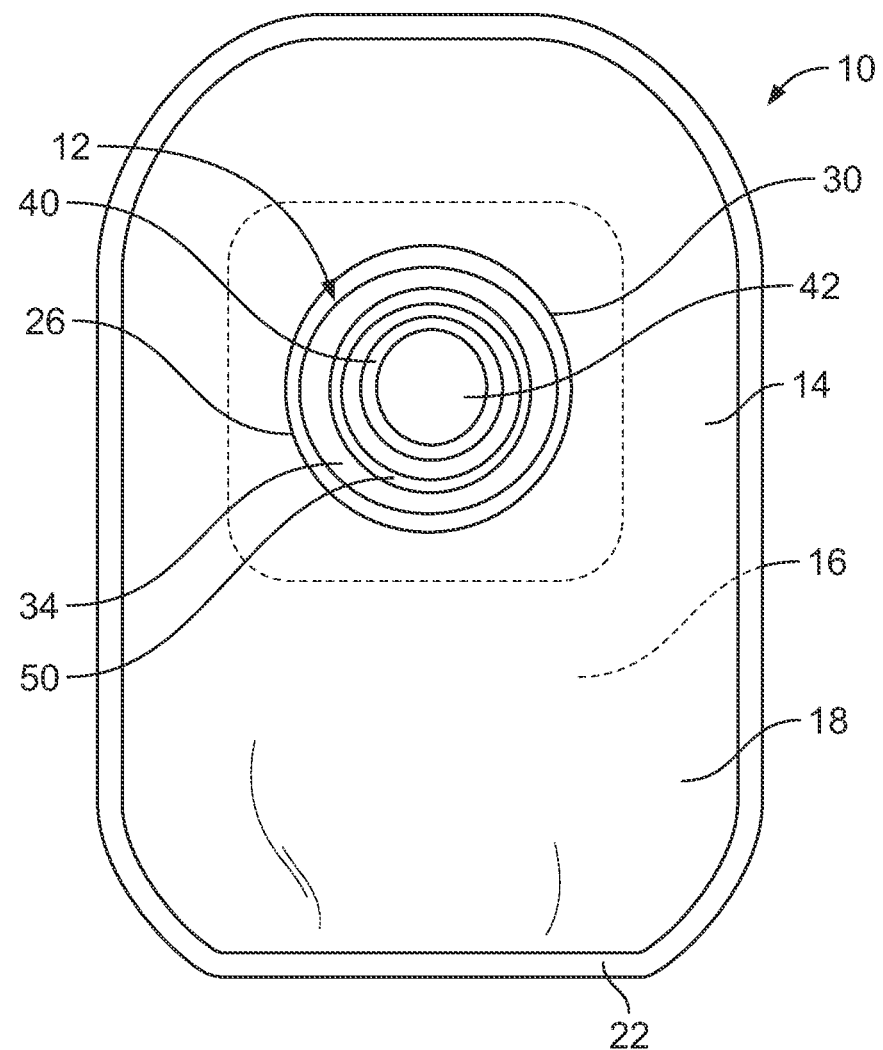
FIG. 1 is a front (user side) view of an embodiment of an ostomy pouch having an internally located mesh collection member.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring now to the figures, there is shown an embodiment of an ostomy pouch 10 having an internally located mesh collection member 12. The pouch 10 has a body 14 formed by, for example, sealing two films to one another about their respective peripheries to define a collection chamber 16. The films can define a user body side wall 18 and a distal or outer side wall 18. The pouch 10 can be of a single-use type and include a sealed bottom wall as illustrated at 22, or the pouch can be of the reusable type and can include an opening at a bottom thereof. The open bottom includes a closure to facilitate emptying the pouch as needed and resealing or closing the bottom for continued use.

The films may be sealed to one another by methods such a heat sealing and the like. If a valve is used, it may be similarly sealed to the pouch 10 at the bottom opening. Suitable methods for sealing the pouch walls/films 18, 20 to one another and the valve to the pouch films will be recognized by those skilled in the art. The pouch 10 may be provided with non-woven layers (not shown) on each of the body and distal side 18, 20 of the pouch 10, or only on the body or distal side of the pouch 10.

Figure 2:
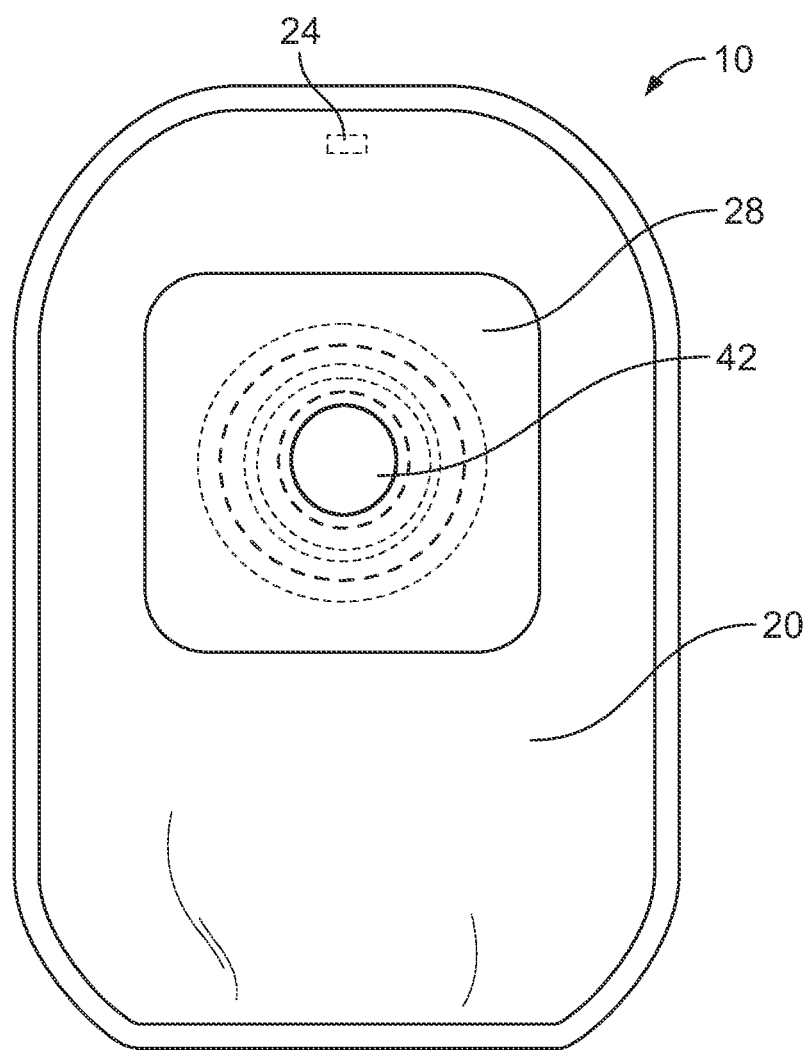
FIG. 2 is an interior view of the ostomy pouch of FIG. 1.

The pouch 10 may include a filter 24, such as the filter shown in FIG. 2. In a configuration the filter 24 is mounted on the distal side 20 wall at a location above the pouch inlet 26.

Figure 3:
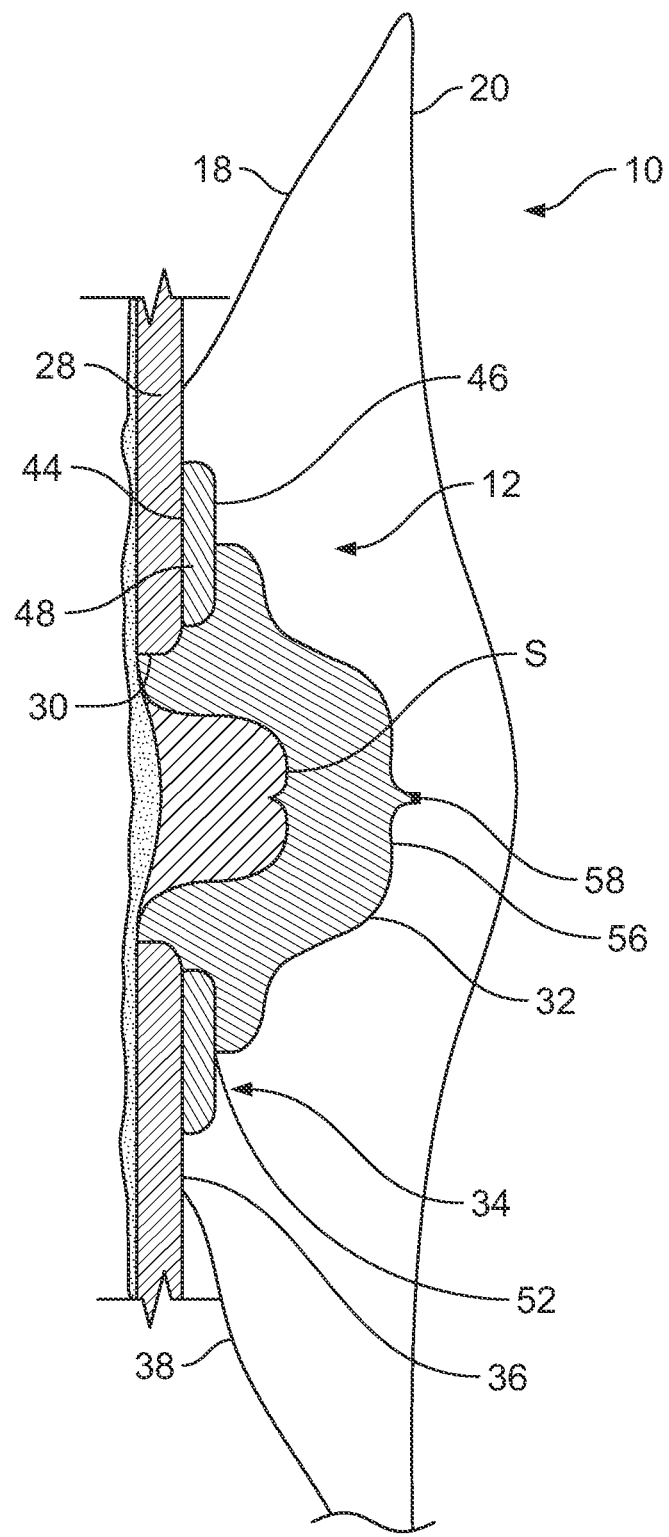
FIG. 3 is a cross-sectional view of a portion of the pouch illustrating the internally located mesh collection member.

In a top section of the pouch 10, the pouch opening 26 is provided in the body side wall through which waste enters the pouch 10 from a stoma S (see, e.g., FIG. 3). A barrier 28 is positioned on the body side wall 18 overlying the opening 26. The barrier 28 includes an inlet opening 30 through which the stoma S extends. The barrier 28 is the material that secures the ostomy pouch 10 to the user and provides a barrier to prevent excretions from contact with the user's peristomal skin. The barrier 28 thus serves two functions—to secure the pouch 10 to the user and to prevent or minimize skin irritation due to excretion contact with the user's skin. The barrier typically includes a skin barrier in addition to an adhesive.

The mesh internal collection member 12 for gas passage is illustrated in FIG. 3 in cross-section with a section of the barrier 28 and a section of the pouch walls 18, 20. The internal collection member 12 includes a thin/ultra-thin, fine net 32, such as a mesh, and a thin capsule 34 in which the net 32 is stored.

The capsule 34 is ring-shaped (see, e.g., FIGS. 1 and 2), and is mounted to a surface 36 of the barrier 28 that faces the outside surface 38 of the body side wall 18; that is, the capsule 34 is mounted to the same surface 36 on which the barrier 28 is mounted to the body side wall 18. The capsule 34 includes an open central region 40 that is aligned with the barrier opening 30 to define a pouch inlet 42. The body side wall opening 26 is sufficiently large that when the barrier 28 is mounted to the pouch side wall 18, the capsule 34 fits within the pouch opening 26 and extends into the pouch 10. That is, the body side wall opening 26 is larger than the outermost diameter of the capsule 34 such that the capsule 34 is positioned inside of the pouch 10 and the barrier 28 operably mounts the capsule 34 to the pouch 10. The barrier 28 is sufficiently large that it fully covers the body side wall opening 26.

The capsule 34 is illustrated in cross-section in FIG. 3. The capsule 34 has a rear wall 44 and a front wall 46 that define a ring-shaped storage chamber 48. In an embodiment, the capsule rear wall 44 is flat and is mounted to the barrier 28. The front wall 46 has a circular circumferential opening 50. The net 32 is paid out through the opening 50. The size or width of the circumferential opening 50 will depend upon the gauge or thickness of the net 32 and can vary (with the thickness of the net 32) as desired.

In an embodiment, the capsule 34 is self-contained. That is, the net 32 is wholly stored within the capsule 34, and is stored in a collected or folded state. A first or open end 52 of the net 32 can be sealed to an surface of the capsule rear wall 44 so that excretions are contained within the net 32 and do not fill into the space within the capsule storage chamber 48. The capsule 34 can be secured to the barrier 28 by adhesive, heat sealing, ultrasonic sealing or other methods that will be recognized by those skilled in the art.

The net 32 is formed as a cylinder and is stored in and extendable from the capsule storage chamber 48 similar to a sausage casing. In an embodiment the net first end 52, which is open for receipt of excretion, is affixed to the capsule 34 at a location such that the net 32 encircles the pouch inlet 42 and the stoma S. The net second end 56 is sealed or closed. The seal 58 can be formed by a tie, heat sealing or other methods that will be appreciated by those skilled in the art.

In an embodiment, the net 32 is stored in the capsule 34 in a collected or folded state. As excretions enters the pouch 10, they enter the pouch (or are discharged into pouch) through the net 32 and pay out the net 32 from the capsule 34. In this manner, the pouch 10 retains its ability to contain a volume of excretion, but at the same time, is not limited in the volume it can contain.

Referring to FIGS. 1 and 3, the circumferential opening 50 can be slightly constricted to prevent the entirety of the net 32 being pulled out at once, however, the opening 50 is not so constricted as create any significant resistance to paying out the net 32. Rather, the weight of the excretions as they enter the net 32 are sufficient to pay out the net 32.

The net 32 is sized (e.g., mesh size) so as to capture solid excretions and allow the passage of gas through the net 32. Capturing the solid excretion prevents the excretion from clogging the filter 24, which could otherwise result in ballooning of the pouch 10. It will be appreciated that as the excretion enters the pouch 10 and is captured in the net 32, any gases entering the pouch 10 will separate from the solid excretion, will pass through the net 32, and exit the pouch 10 through the filter 24. In addition, capturing the solid excretion will also facilitate directing the excretion to the bottom of the pouch 10, thus allowing more efficient use of the ostomy pouch 10.

It is anticipated that the capsule 34 can be formed from any polymeric material that is compatible with use in an ostomy product and the expected input as well as the method used to secure the capsule 34 to the barrier 28. The net 32 can be formed of a wide variety of materials that can be formed into a mesh, such as nylon and other polymeric and natural materials, again, compatible with use in an ostomy product. In a construction in which the pouch 10 is a two-piece pouch, the use of the present mesh collection member 12 can facilitate emptying of the pouch 10, in that the excretions are contained within the net 32.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. An ostomy pouch, comprising:
a body side wall and a distal side wall defining a collection chamber therebetween;
an opening provided in the body side wall;
a barrier operably mounted to the body side wall over the opening, the barrier having an inlet opening; and
an internal collection member mounted to the barrier, the internal collection member including a tubular net having a first open end and a second closed end, and a ring-shaped capsule for storing the net, the ring-shaped capsule having an open central region, the net being stored in the ring-shaped capsule in a collected manner, the ring-shaped capsule mounted to the barrier with the ring-shaped capsule open central region and the barrier inlet opening aligned with one another to define a pouch inlet, the ring-shaped capsule extending into the pouch collection chamber, the first open end of the net mounted to the ring-shaped capsule overlying the pouch inlet,
wherein the ring-shaped capsule comprises a front wall with a circumferential opening adjacent to the open central region, and a rear wall and wherein excretion is inlet to the pouch and is discharged into the net, paying out the net from the ring-shaped capsule through the circumferential opening, and wherein gas with excretion that is inlet to the pouch passes through the net and into the collection chamber.

2. The ostomy pouch of claim 1, wherein the rear wall is flat.

3. The ostomy pouch of claim 1, wherein the net is formed from a mesh.

4. The ostomy pouch of claim 1, wherein the first open end of the net is secured to an interior surface of the ring-shaped capsule.

5. The ostomy pouch of claim 1 further including a filter, and wherein gas inlet to the pouch with the excretion passes through the net and is discharged from the pouch through the filter.

6. The ostomy pouch of claim 5, wherein the filter is on the distal wall.

* * * * *